United States Patent [19]
Latterell et al.

[11] Patent Number: 5,814,090
[45] Date of Patent: Sep. 29, 1998

[54] IMPLANTABLE MEDICAL DEVICE HAVING HEAT-SHRINK CONFORMING SHIELD

[75] Inventors: Scott T. Latterell, Minneapolis; Dennis Brumwell, Bloomington, both of Minn.

[73] Assignee: Angeion Corporation, Minneapolis, Minn.

[21] Appl. No.: 751,836

[22] Filed: Nov. 18, 1996

Related U.S. Application Data

[63] Continuation-in-part of Ser. No. 486,759, Jun. 7, 1995.

[51] Int. Cl.⁶ .................................................. A61N 1/375
[52] U.S. Cl. ................................................................ 607/36
[58] Field of Search .................................. 607/36, 5, 6, 7, 607/8, 37

[56] References Cited

U.S. PATENT DOCUMENTS

| | | |
|---|---|---|
| 3,735,766 | 5/1973 | Bowers et al. ............................ 607/36 |
| 3,924,640 | 12/1975 | King ........................................... 607/36 |
| 4,041,955 | 8/1977 | Kelly et al. ................................ 607/36 |
| 5,529,579 | 6/1996 | Alt et al. .................................... 607/36 |

*Primary Examiner*—Scott M. Getzow

[57] ABSTRACT

An implantable medical device, such as an implantable cardioverter defibrillator (ICD), utilizes a heat-shrink conforming shield to substantially isolate internal components and circuitry from the device housing and from each other. Preferably, the shield also protects the internal circuitry of the device from undesirable electro-magnetic coupling effects. The shape conforming isolation material provides an inexpensive, effective isolation barrier that helps shield the circuitry from undesired coupling effects and also protects the components from inadvertent shorts as well as potential damage during assembly and testing.

12 Claims, 6 Drawing Sheets

Fig. 1

PRIOR ART

IMPLANTABLE MEDICAL DEVICE HAVING HEAT-SHRINK CONFORMING SHIELD

RELATED APPLICATION

The present invention is a continuation-in-part application of a co-pending U.S. patent application entitled "SHIELD FOR IMPLANTABLE CARDIOVERTER DEFIBRILLATOR", Ser. No. 08/486,759, filed Jun. 7, 1995, which is assigned to the assignee of the present invention and the disclosure of which is hereby incorporated by reference.

FIELD OF THE INVENTION

The present invention relates to implantable medical devices and, more particularly, to a heat-shrink conforming shield for implantable cardioverter defibrillators having internal circuitry subject to adverse capacitive coupling effects.

BACKGROUND OF THE INVENTION

Cardiac muscle fibrillation is the rapid and asynchronous contraction of individual muscle fibers in the heart. The result is a slightly quivering and non-functional heart muscle. When fibrillation occurs within the lower chambers of the heart or ventricles, blood flow ceases and, if not corrected within minutes, death of the patient will result. Fibrillations occurring only in the upper chambers of the heart or atria results in decreased cardiac output that may be symptomatic to the patient. Other forms of cardiac arrhythmia include ventricular or supraventricular tachycardia, which are very rapid, organized/synchronous muscle fiber contractions that impair cardiac output to lesser or greater degrees dependent on cardiac refill times and preload pressures.

Implantable cardioverter and defibrillator (ICD) systems attempt to treat cardiac arrhythmias by passing through the heart muscle a cardioversion or defibrillation countershock, depending on the type of cardiac arrhythmia diagnosed. The objective of the cardioversion or defibrillation countershock is to immerse as much of the myocardium as possible within the electrical field generated by the countershock. The countershock is a truncated capacitive discharge of electrical energy that generally ranges from 0.1 to 5.0 Joules for cardioversion and from 5 to 40 Joules for defibrillation of the ventricles.

U.S. Pat. No. 4,774,950, the disclosure of which is incorporated herein by reference, discloses an embodiment of an abdominally implanted ICD. U.S. Pat. No. 5,405,363, the disclosure of which is also incorporated herein by reference, describes embodiments of a smaller, pectorally implanted ICD.

Conventional abdominally implanted ICDs include a metal housing that floats with respect to the internal electronic circuitry. The housing is not physically secured to the internal electronics and is tied to the battery ground through a high impedance, typically 200K ohms. This is desirable to prevent the housing from acting as an electrode and thereby siphoning off current that should flow between the two defibrillation electrodes. Preventing the housing from acting as an electrode at an abdominal location is especially desirable, to avoid diverting current from the heart. Even though the housing is essentially floating, the housing acts as a shield against electromagnetic interference and protects the internal electronic circuitry from picking up induced pulses from stray electromagnetic fields.

Unlike abdominally implanted ICDs, pectorally implanted ICDs, such as described in U.S. Pat. No. 5,405,363, typically use the housing as one of the electrodes. When the housing is used as an electrode, implanting the housing in the pectoral region on the patient's left side and inserting a transvenous electrode into the patient's right ventricle will cause the defibrillation current to be directed along a very desirable vector. This results in a lower defibrillation threshold, that is, a lower minimum energy to produce successful defibrillation.

A common approach to delivering shocks with an ICD is to divide the shock into more than one phase. With biphasic waveforms, the polarity of the second phase is opposite of that of the first phase. It has been consistently lower voltage and energy requirements than monophasic waveforms of the same duration. With biphasic waveforms, the two electrodes of the defibrillator change polarities between phases.

When using a pectorally implanted housing as an electrode for biphasic-waveform shocks, the housing must be switched from one polarity of the output capacitor to the opposite polarity. In this case, the housing of the device cannot serve as an electrode simply by tying the housing to one of the battery electrodes, as it could be done for a monophasic pulse. When the housing is configured as an electrode for pectorally implanted ICD delivering a biphasic waveform, the housing acts as a large, first plate of a capacitor, and the other conductors in the circuitry of the ICD act as a second plate of the capacitor. When the housing voltage suddenly changes, voltages and currents are induced on nearby conductors. These induced currents and voltages potentially can be of sufficient magnitude so as to introduce unwanted logic signals or switching signals in the circuitry of the ICD, which have the possibility of causing circuit malfunctions and consequent harm to the patient.

For circuits with conductors having significant length, or lying adjacent to the housing, this kind of capacitive coupling effect is magnified. Such conductors are common in ICDs having interconnect wiring between various parts of the circuit, for example. These conductors often are in a medium know as "flex tape," wherein conductive paths are printed on a flexible dielectric film that is wrapped, folded and bent to reach various points of the circuit to which connections must be made. Often, the most convenient route for the flex tape to reach these various points is around the outside of the electronics core, that is, near the inside surface of the housing thereby increasing the likelihood of undesirable capacitive coupling.

As ICDs become smaller, especially pectorally implanted ICDs, the interconnect conductors and electronics are positioned nearer to the inside housing surface of the device. When the housing of the ICD is used as a switchable electrode, it is no longer possible to couple the housing to ground, for example, to allow the housing to serve as a capacitor coupling shield. Consequently, capacitive coupling problems that have not been experienced in the past are impacting the design and operation of new ICDs. These unanticipated capacitive coupling problems limit the miniaturization and effective operation of such devices. In addition, the problem of shorting and inadequate isolation of component parts and circuit paths from each other and from the housing are also complicated as the size of the ICD is decreased.

Most other types of implantable medical devices, such as abdominally implanted ICDs and drug pumps, today employ molded plastic frames and/or liners to position, protect and isolate the circuitry and other components within the housing of the device. As the demand for smaller devices increases, the design of such frames becomes harder and more expensive. One solution is to essentially eliminate the frame portion of the medical device; however, when this is done it increases the possibility of damage to internal device components due to handling during the manufacturing process of the medical device.

A possible solution which has been proposed is to encapsulate the circuitry of an implantable medical device within a vacuum-molded, two-piece clam shell liner, instead of using the traditional plastic frame. While this technique helps reduce the size of the device, the use of a pair of plastic sheets in this manner is mechanically challenging for a number of reasons. First, the plastic sheets are very limp and can be difficult to work with during the manufacturing process. Second, during the vacuum-molding process the plastic sheets are stretched to fit the exterior contours of the device. This stretching thereby creates thin spots and potential openings in the plastic sheets in those areas where protrusions or other features on the surface of the device do not conform to the initial shape of the plastic sheet. This thinning is not desirable because it may reduce the amount of insulative and mechanical protection at points where this is required or which may be more likely to be subject to wear within the housing of the device. Third, the use of a vacuum-molding process necessarily subjects the components of the device to increased mechanical stress during assembly. Finally, the use of a two-piece assembly leaves edges which must be properly trimmed and overlapped. This, along with the tolerance issues associated with intricately mating parts, creates a design that is subject to tearing and separation during further handling of the device.

While current packaging and isolation techniques have been adequate for existing abdominally implanted ICDs and other medical devices, it is desirable to provide an improved packaging system for the internal components of a pectorally implanted ICD that can both protect and isolate those components without substantially increasing the total volume of the ICD.

SUMMARY OF THE INVENTION

The present invention is an implantable medical device, such as an implantable cardioverter defibrillator (ICD), which uses a heat-shrink conforming shield to substantially isolate internal components and circuitry from the device housing and from each other. Preferably, the shield also protects the internal circuitry of the device from undesirable electro-magnetic coupling effects.

The implantable medical device has a housing comprising a biocompatible material. Circuitry, which is susceptible to undesirable capacitive coupling effects, for example, is positioned within the housing. In the case of an ICD, the circuitry controls delivery of cardioversion/defibrillation countershocks, and an energy source is provided coupled to the circuitry as is a capacitive energy storage system. A first shape conforming isolation material which encapsulates the circuitry, the energy source and the capacitive energy storage system is provided inside the housing of the ICD. A thin layer of conductive shielding material surrounds the first shape conforming material and a second shape conforming material encapsulates the thin layer of shielding material. The shape conforming shield provides an inexpensive, effective isolation barrier that helps shield the circuitry from undesired coupling effects, inadvertent shorts and component defects caused during the manufacturing process.

DETAILED DESCRIPTION OF THE PREFERRED EMBODIMENT

Figure 5:
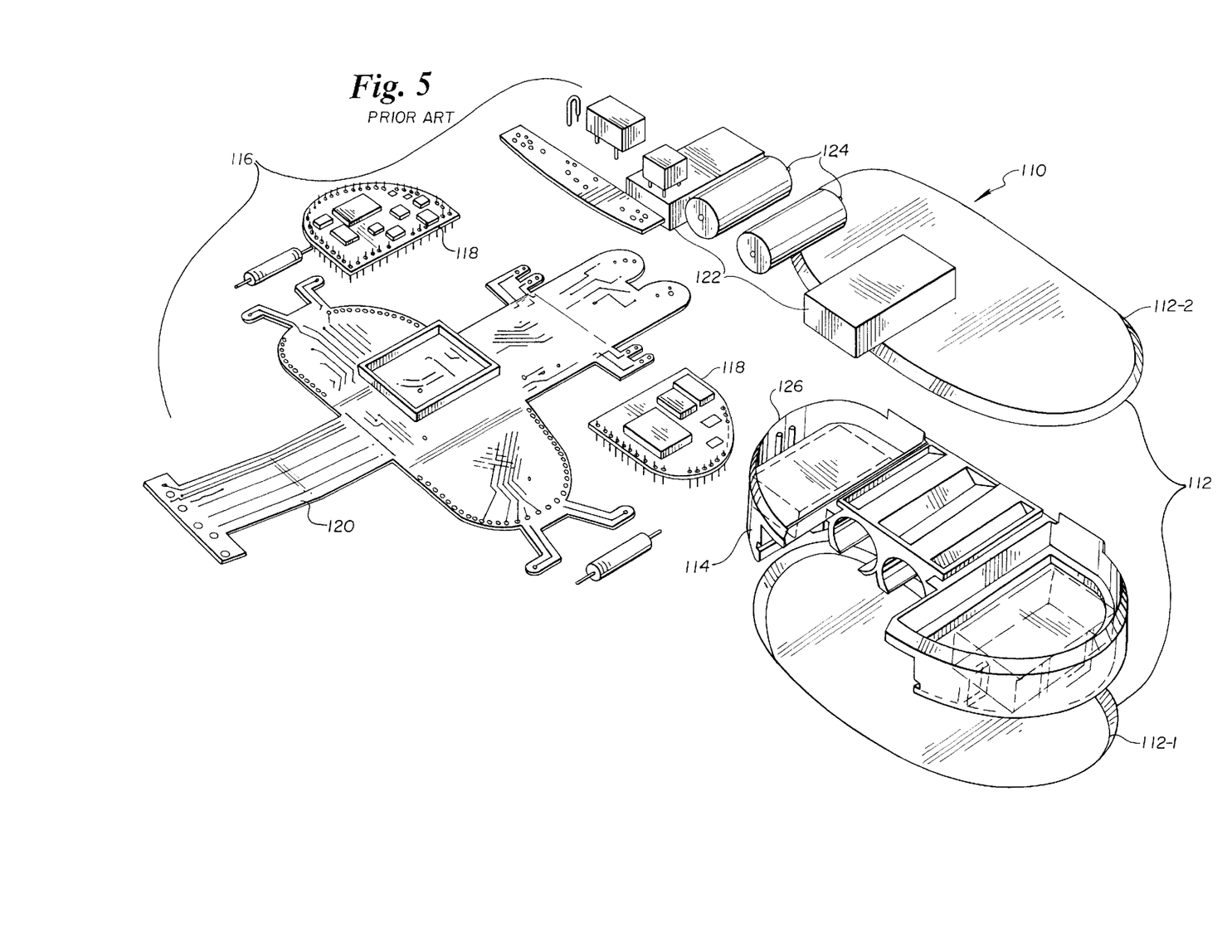
FIG. 5 is a perspective exploded view of an abdominally implantable prior art implantable cardioverter defibrillator (ICD).

FIG. 5 illustrates an early version of a known implantable cardioverter defibrillator (ICD) 110 which is implantable in a patient's abdomen. ICD 110 includes a housing 112 preferably formed in two sections, 112-1 and 112-2, and a plastic frame member 114 which holds the circuitry 116 of the device. Circuitry 116 preferably includes electronic circuit boards 118 which are connected by a flex tape connector 120 and mounted within frame member 114. In addition, a pair of battery cells 122 and a pair of electrolytic capacitors 124 are also connected to flex tape connector 120 and mounted within appropriate cavities within frame 114. Feedthroughs 126 provide electrical connection of the circuitry 116 within housing 112 to a header (not shown) into which various sensing and defibrillation electrode leads may be connected.

Because ICD 110 is implanted in a patent's abdomen, the housing 112 is not utilized as an electrode for purposes of delivering high voltage defibrillation countershocks. In addition, while it is desirable for ICD 110 to be made as small as possible for ease and comfort of implantation in the patient's abdomen, there are no particular size requirements that constrain the choice of packaging techniques used to construct ICD 110. Accordingly, the packaging of ICD 110 employs a conventional technique of using a plastic frame 114 in which to mount and secure the various components of circuitry 116 within the housing 112.

Figure 1:
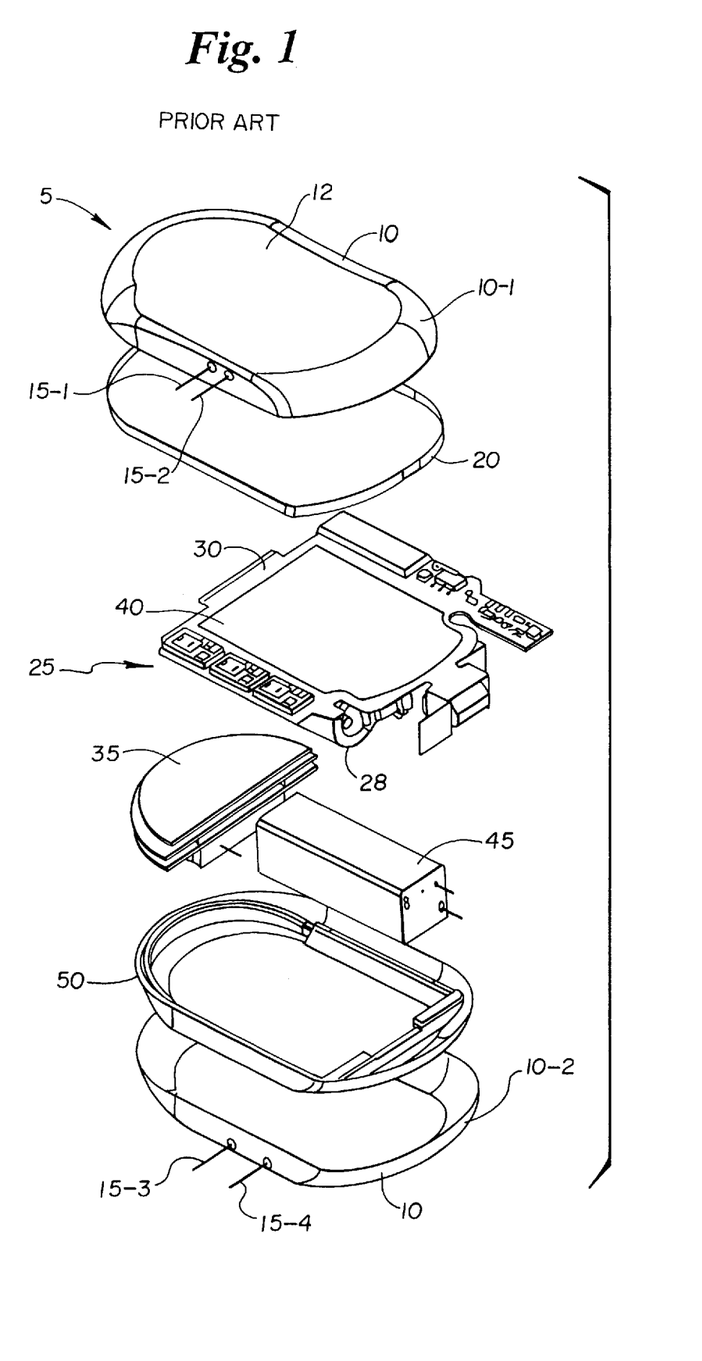
FIG. 1 is a perspective exploded view of a prior art implantable cardioverter/defibrillator.

FIG. 1 illustrates a more recent version of an ICD known in the art which is designed to be implanted in the pectoral region. ICD 5 includes a housing preferably formed in two sections 10-1, 10-2, joined together by a weld ring 20. Of course, single-piece and multi-piece housings having more than two housing sections also are contemplated. Housing 10 preferably is formed of biocompatible material, such as titanium alloy, but also can be formed of other biocompatible metallic or non-metallic conductive materials.

Positioned within housing 10 is circuitry 25, which controls delivery of countershocks to the myocardium of a patient in a known manner. Circuitry 25 includes electronic circuit board assembly 35 and flex tape interconnect conductor assembly 30, which are susceptible to undesirable electromagnetic coupling effects of origin external to circuitry 25. Such undesirable coupling effects can include capacitive coupling effects between housing 10 and circuitry 25, for example, when housing 10 is used as an electrode.

Additionally, other electromagnetic coupling effects of origin external to the ICD and/or external to the patient can induce unwanted currents and voltages within circuitry 25, leading to malfunction of the ICD and possible consequent harm to the patient.

Circuitry 25 includes at least one capacitor 28 for storing electrical energy to generate the cardioversion/defibrillation countershocks applied to the myocardium of the patient. Although only one such capacitor 28 is shown in FIG. 1, two or more such capacitors also are contemplated by the invention. Of course, a wide variety of different types of capacitors can be used with the ICD according to the invention, including double layer, electrolytic, and electrostatic capacitors. Double layer capacitors have no permanent dielectric, electrolytic capacitors have a permanent dielectric formed on the surface of a metal electrode, while the opposing electrode is an electrolyte, and electrostatic capacitors have a permanent dielectric and two metallic electroplates. Any type of capacitor capable of storing electrical energy to generate the cardioversion/defibrillation countershocks to be applied can be used, according to the invention.

Housing 10 preferably includes plastic insulator 50, which serves to prevent undesired electrical communication between housing 10 and circuitry 25. Further, feedthroughs 15-1–15-4 extend transversely to the surface of housing 10 to provide electrical connection between ICD 5 and a plurality of leads, such as high-voltage electrodes, and pacing and sensing electrodes for the atrium and ventricle, for example, which are unmarked, through a connector port housing (not shown).

Also disposed within housing 10 is an energy source 45, which is coupled with circuitry 25. Energy source 45 preferably is a battery for providing electrical energy to circuitry 25 for the delivery of countershocks to the myocardium of the patient. Of course, a wide variety of energy sources 45 can be used such as lithium/vanadium oxide batteries, as well as lithium/silver vanadium oxide, solid cathode, liquid organic electrolyte batteries, and other batteries capable of operating at low current drains for long periods of time, and capable of then providing high-current pulses when defibrillation is required. Typically, the high-current pulses are in excess of two amperes at voltages above two volts, for periods of as long as ten seconds. The battery cell used, therefore, preferably exhibits high energy density, high current-delivery capability, and low self-discharge. The battery also should meet the applicable safety and reliability standards required of all implantable power sources and have a discharge curve providing a state of charge indication that can signal the need for replacement of the device. Additionally, more than one battery or more than one battery chemistry may be used.

In addition to energy source 45 and one or more capacitors 28, circuitry 25 preferably includes a power transformer to step up the voltage of energy source 45 to a higher voltage for storage on capacitor 28, and also includes at least one switch and diode, as is well known in the art. This high-voltage output circuitry transfers energy stored in the high-voltage capacitor(s) to the heart. The circuitry should perform this transfer function with minimal wasted energy, because implantable batteries and capacitors have limited energy capacity. In addition to the high voltage output circuitry, appropriate sensing and control circuitry are also included in circuitry 25.

To shield circuitry 25 against the undesirable coupling effects to which it is susceptible, ICD 5 includes conductive shield 40, disposed between housing 10 and circuitry 25. Conductive shield 40 preferably is metallic and can be integrated directly onto flex tape interconnect assembly 30, so that the conductor paths of flex tape interconnect assembly 30 lie underneath shield 40. Shield 40 thus shields flex tape interconnect assembly 30 against undesirable coupling effects between assembly 30 and objects external to assembly 30, such as housing 10 when housing 10 is used as an electrode. Of course, shield 40 also shields electronic circuit board assembly 35 against undesirable coupling effects as well.

Figure 2:
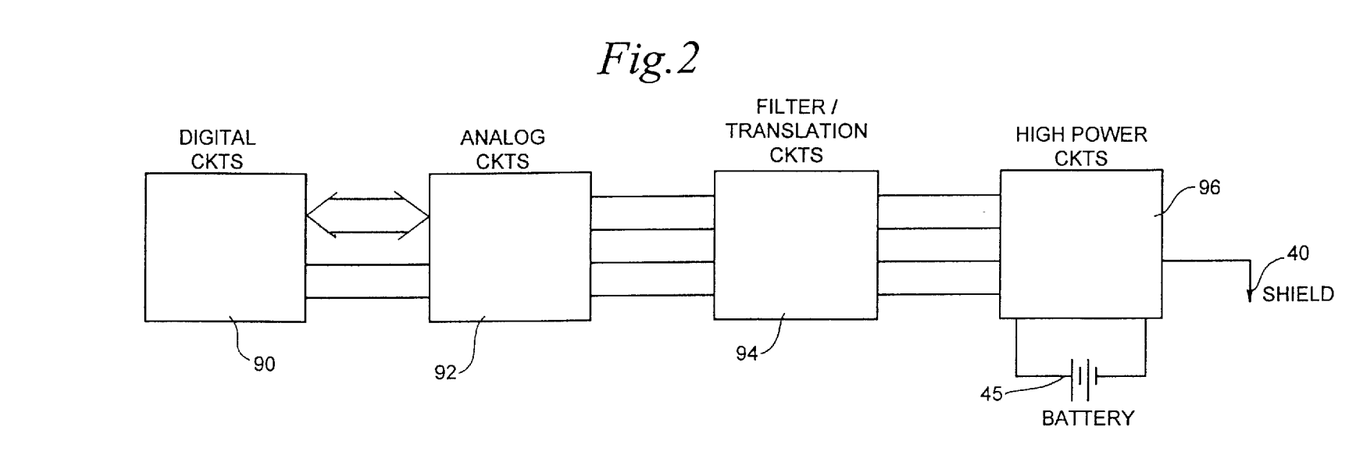
FIG. 2 is a circuit diagram showing elements of the FIG. 1 defibrillator.
Figure 3:
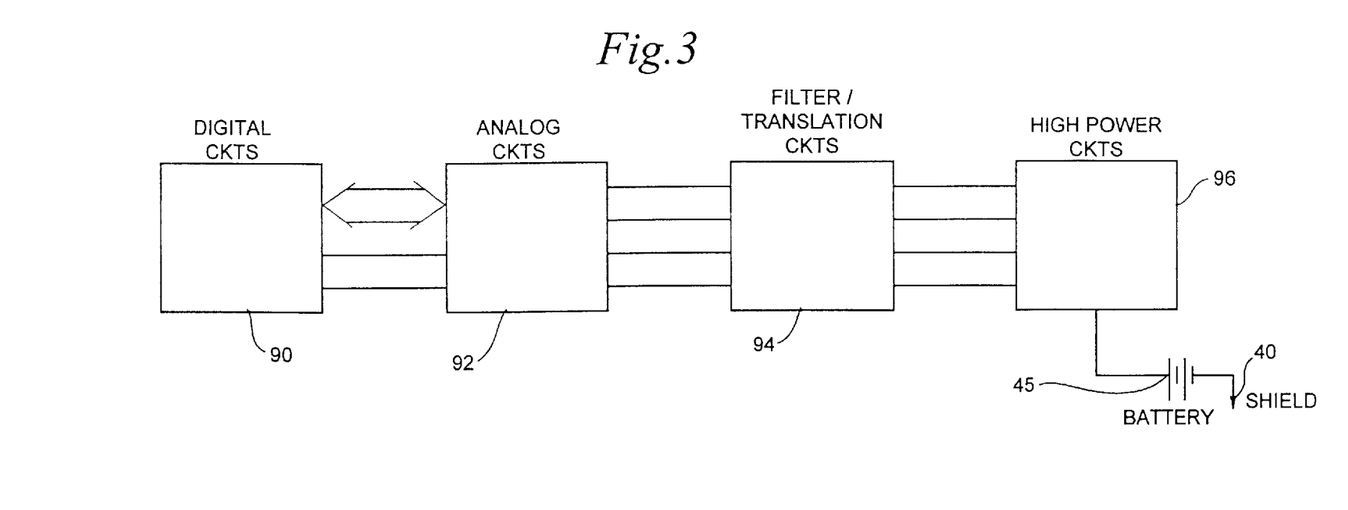
FIG. 3 is a circuit diagram showing elements of the FIG. 1 defibrillator according to an alternative embodiment.

FIGS. 2–3 are circuit diagrams showing elements of the FIG. 1 defibrillator. Digital circuitry 90, analog circuitry 92, filter/translation circuitry 94 and high power circuitry 96 are in electrical communication as shown in FIGS. 2–3. Conductive shield 40 is in electrical communication with a reference point, which now will be further described. According to the FIG. 2 embodiment, the reference point is a battery ground, that is, shield 40 is indirectly connected to the ground plane through high power circuitry 94. According to the FIG. 3 embodiment, the reference point is on battery 45 itself, preferably on the high side of the battery. Connecting shield 40 to the reference point enables conductive shield 40 to shield circuitry 25 against the previously described undesirable coupling effects by acting as a ground plane for undesired electromagnetic radiation. Of course, the reference point also can be disposed at other points, such as any point in the circuit that passes high frequency current efficiently to the average circuit potential. This includes capacitive or direct connections to the defibrillator battery or even the high voltage capacitors.

Figure 4:
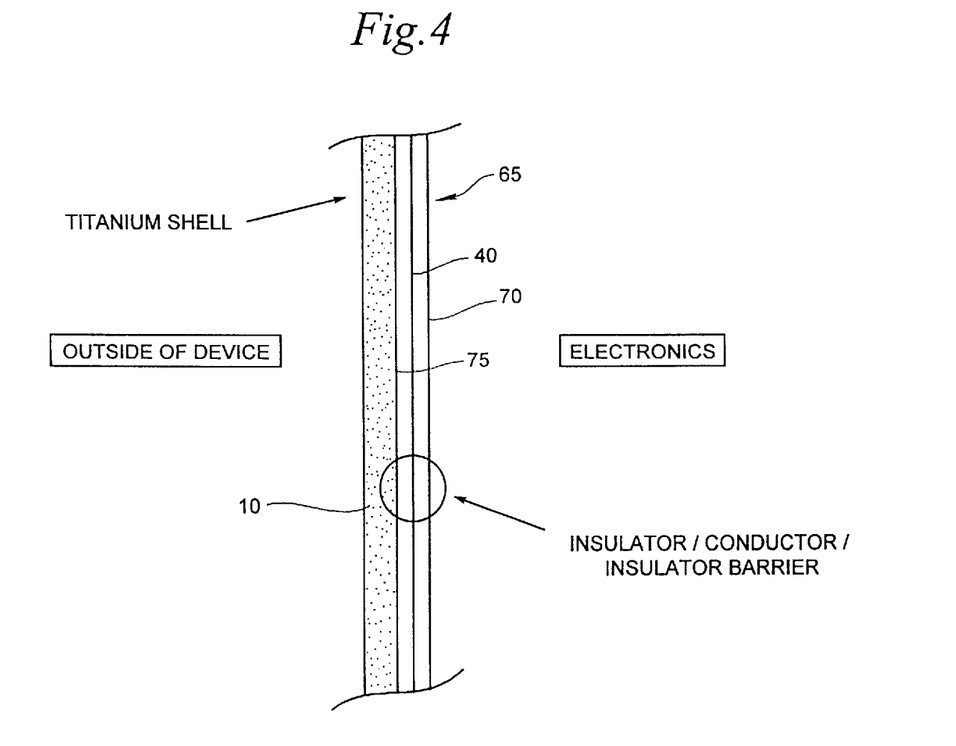
FIG. 4 is a cross-sectional view of an ICD housing and shield according to one embodiment of the invention.

According to the ICD embodiment of FIG. 4, conductive shield 40 is embedded in liner 65, preferably formed of a plastic that covers the entire inner surface of housing 10. According to this embodiment, the entire area inside housing 10 is shielded from capacitive coupling effects due to housing 10, and from electromagnetic coupling effects of origin external to ICD 5. Plastic liner 65 preferably includes inner insulative material 70 and outer insulative material 75, between which conductive shield 40 is disposed. As with previous embodiments, conductive shield 40 preferably is electrically connected to the system ground or to some other reference point. Although this embodiment is advantageous in that it shields the entire interior of housing 10, not just circuitry 25, this embodiment requires ICD 5 to be of slightly larger dimensions.

Preferably, the FIG. 4 embodiment according to the invention is of composite, three-ply sandwich insulator-conductor-insulator construction. According to an alternative embodiment, however, liner 65 can be of two-sheet construction, in which one of insulative layers 70, 75 includes a sputtered surface forming conductive shield 40. For example, outer insulative layer 75 can include a sputtered inner surface, or inner insulative layer 70 can include a sputtered outer surface, and inner insulative layer 70 or outer insulative layer 75, respectively, can be formed as a separate layer. The insulator-shield-insulator arrangement preferably is thermoformed into liners 65, as shown in FIG. 4. Upon assembly, liners 65 would overlap and be electrically connected one to the other or through the device circuitry 25.

Insulative layers 70, 75 preferably are formed of a thin (less than 0.010 inch) thermoformable film that is at least moderately tear and puncture resistant and that has a minimum 2,000 volt dielectric strength. Conductive shield 40 can be formed of copper, aluminum or other similar conductive materials, and preferably has a resistance of less than 10 ohms over a 3.5 inch length of sheet 2.5 inches wide.

Shield 40 supports 2 amp pulse current at a voltage of 20 volts, according to a preferred embodiment. Shield 40 need not be solid; a fine mesh grid also will perform satisfactorily. For example, the microcracks to be expected by forming a sputtered metal would perform as a grid system. Electrical connection to internal circuitry 25 preferably is through a wire that is soldered, welded, or otherwise attached to a point on the flex circuit. Of course, other suitable connection arrangements also are contemplated by the invention.

As discussed in great detail in the '363 patent, unlike abdominally implantable ICD 110 as shown in FIG. 5, ICD 5 as shown in FIG. 1 has definite size limitation in order to allow for implantation of the device in the pectoral region. As a result, one of the changes made in order to reduce the size of ICD 5 was to eliminate the use any kind of frame member 114 as shown for ICD 110 in FIG. 5 for mounting and securing the circuitry 116. Although this decreases the internal volume of ICD5, the lack of a frame member presents new problems were not encountered in prior ICDs, such as ICD 110. First, without a frame member there is an increased possibility of inadvertent shorts within the circuitry 25 when there is no frame member 114 into which the circuitry can be secured. Because circuitry 25 is essentially floating within housing 10, there is also the chance of portions of circuitry 25 coming into contact with housing 10, therebypossibly creating an inadvertent short within circuitry 25. To decrease this possibility, a shield can be inserted between circuitry 25 and housing 10 as previously disclosed in the embodiment of the invention shown in FIG. 4. Second, the lack of any kind of frame member complicates the manufacturing build process and increases the possibility of damage to the circuitry 25 as a result of inappropriate handling during assembly. Because flex tape connector 40 is not rigid, it is more difficult to handle during assembly and testing. Consequently, special handling and testing procedures and precaution must be implemented during assembly and testing of circuitry 25.

Other than increased patient comfort and ease of implantation, one of the most significant advantages of implantation of ICD 5 as shown in FIG. 1 in the pectoral region is the fact that the housing 12 can be used as one of the defibrillation electrodes. Unlike ICD 110 shown in FIG. 5 which was designed for implantation in the abdomen, and in which housing 112 was not used as an electrode and could serve as a ground plane shield to protect circuitry 116 from the high voltage, high current defibrillation countershocks, the housing 10 of ICD 5 includes at least a portion of which is a conductive electrode and hence cannot be used as a ground plane shield. As a result, circuitry 25 is succeptible to undesirable electromagnetic coupling effects, particularly during delivery of the high voltage, high current defibrillation countershocks. Additionally, other electromagnetic coupling effects external to the ICD 5 and/or patient may also induce unwanted currents and voltages within circuitry 25. To counteract such undesirable electromagnetic coupling effects, ICD 5 utilizes a shield as disclosed in the previously described.

Figure 6:
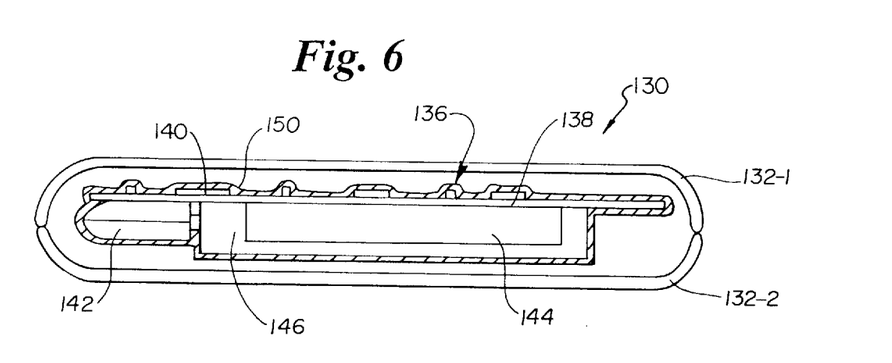
FIG. 6 is a cross sectional view of an ICD having a first shape conforming isolation material according to the present invention.

In a preferred embodiment the present invention, as shown in FIG. 6, the circuitry 136 of an implantable medical device 130, such as ICD 5, is encapsulated by a shape conforming isolation material 150. Shape conforming isolation material 150 is used to provide a quick and inexpensive way to reduce undesirable coupling effects to circuitry and components on flex circuit 140 and circuit boards 138 so as to prevent shorts and to reduce the possibility of damage to circuitry and components during assembly and testing of the device. Shrink-wrap shape conforming isolation material 150 is preferably a pre-formed/one-piece boot or sock having at least one opening into which the circuitry 136 is placed. It will be recognized that a multipiece boot, such as two mated socks, could also be used. Alternative low temperature thermoplastic shrink materials such as neoprene, polyvinyl or polyester thermoplastic, or any equivalent shrink wrap, isolation material could also be utilized without departing from the scope of the present invention. It should be understood that shape conforming material 150 is considered to encapsulate the circuitry and components of circuitry 136, even if the edges of shape conforming material 150 do not entirely seal together. Obviously, electrical connections to feedthroughs 148 will need to extend out of shape conforming material 150. It should also be understood that larger components, such as batteries 142, 144 or capacitors 146 may or may not be encapsulated within shape conforming material 150, and, accordingly, electrical connections to these components may extend beyond shape conforming material 150. The primary goal of the present invention is to conveniently isolate and protect circuit boards 138 and flex circuit 140. Advantageously, shape conforming material 150 increases, rather than decreases, the thickness of isolation material resulting in a significantly decreased chance of thin spots or voids. Preferably, shape conforming material will be shrunk to fit snugly around circuitry 136 in response to application of a heat source. Alternatively, other shape conforming catalysts or processes could be utilized, such as infra-red or ultra-violet radiation.

Figure 7:
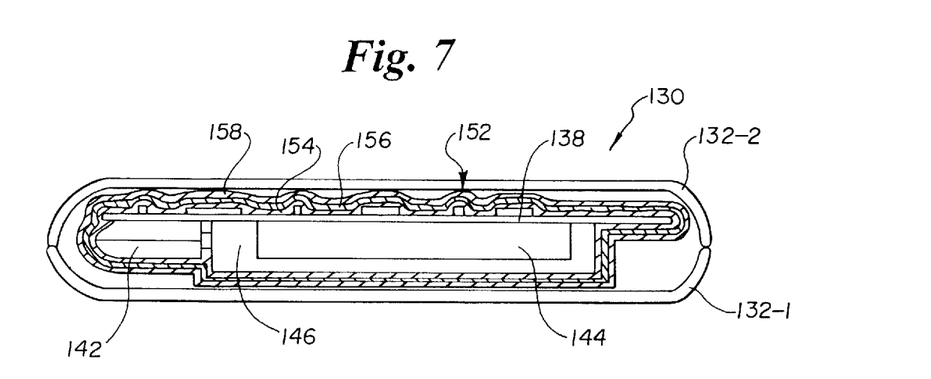
FIG. 7 is a cross sectional view of an ICD similar to FIG. 6 having a shape conforming isolation material according to an alternative embodiment of the present invention.

An alternative embodiment of the present invention is illustrated in FIG. 7. In this embodiment, a shape conforming assembly 152 is illustrated encapsulating circuitry 136, including circuit boards 138, flex circuit 140, batteries 142, 144 and capacitors 146. Shape conforming assembly 152 comprises a first shape conforming isolation material 154, a thin layer of conductive shielding material 156 and a second shape conforming isolation material 158. Shielding material 156 may be used in place of a separate shield, or may be used in addition to a separate shield within ICD 130 to provide shielding against undesired electromagnetic coupling effects. Preferably, shielding material 156 is a conductive metal, such as copper or aluminum, although other forms of conductive shielding materials could be utilized, such as a mesh grid or braid, or a conductive polymer. Alternatively, an inner surface of second shape conforming isolation material 158 or an outer surface of first shape conforming isolation material 154 could be coated with a conductive layer, such as by deposition, thin film techniques or chemical adhesion or the like. Preferably, shielding material 156 is relatively thin so as to allow it to mold around the circuitry 136 in position between shape conforming isolation materials 154 and 158.

In one embodiment, shielding material 156 is on the order of less than 0.25 mm thick and shape conforming materials are on the order of less than 1.0 mm thick. Shape conforming materials 154 and 158 may be made of the same material and thickness, although it is preferably contemplated that different materials and different thickness of shape conforming materials may also be utilized such that second shape conforming material has a higher dielectric constant and the first shape conforming material is mechanically stronger (e.g., higher shear strength and modulus of elasticity and/or increased thickness). In addition, it is possible to vary the thickness of any or all of the shape conforming materials 154 and 158 and the shielding layer 156 at strategic locations around the periphery of circuitry 136, depending upon the location of key interfaces between circuitry 136 and housing 132 or upon the orientation of circuitry 136 (e.g., the surface of circuitry 136 facing the heart may be provided with thicker layers).

Figure 8:
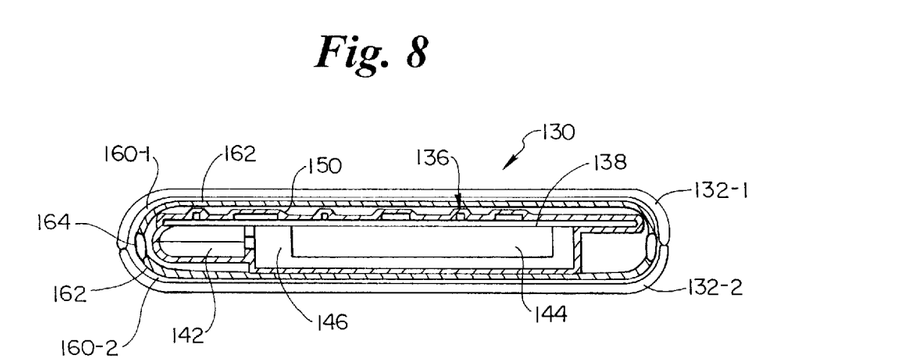
FIG. 8 is a cross sectional view of an ICD similar to FIG. 6 showing another alternate embodiment of the present invention.

Another alternate embodiment of the present invention is shown in FIG. 8 in which the embodiment of isolation material 150 as shown in FIG. 6 is positioned within a housing 132 that includes an isolation layer 160 comprised of isolation materials 160-1 and 160-2 and shield layer 166 interposed therebetween. In this embodiment, isolation layers 160-1 and 160-2 are each adhered to an inner surface of one housing half 132-1 and 132-2, such as by bonding the material onto the inner surface of housing halves 132-1 and 132-2. Alternatively, isolation layer 160 may be built up on the interior of each housing half 132-1 and 132-2 by using spraying, thin film or vapor deposition techniques or the like. In this embodiment, isolation materials 160 may be any of the heat-shrink insulative materials previously described, as well as similar insulative materials which are capable of being deposited onto and adhering to the inner surface of housing halves 132-1 and 132-2. To accommodate mating of the two housing halves 132-1 and 132-2, shield layer 162 is smaller in surface area than either isolation material layers 160. Preferably, the isolation material 160 covers weld ring 164 to form a protective overlap, but the shield layer 162 does not cover weld ring 164.

We claim:

1. An implantable cardioverter defibrillator (ICD) device capable of subcutaneous positioning within a patient, the implantable cardioverter defibrillator comprising:
   a housing comprising a biocompatible material at least a portion of which is conductive and used as an electrode for the ICD device;
   circuitry positioned within the housing to control delivery of cardioversion/defibrillation countershocks, wherein the circuitry is susceptible to undesirable coupling effects;
   an energy source coupled to the circuitry;
   a capacitive energy storage system coupled to the energy source and the circuitry;
   a first shape conforming isolation material encapsulating the circuitry inside the housing,
   a thin layer of conductive shielding material surrounding the first shape conforming isolation material; and
   a second shape conforming isolation material encapsulating the thin layer of shielding material.

2. The device of claim 1 wherein the first shape conforming material encapsulates the energy source and the capacitive energy storage system.

3. The device of claim 1 wherein the housing includes a portion which is utilized as an electrode operatively coupled with the circuitry to deliver the cardioversion/defibrillation countershocks.

4. The device of claim 1 wherein each shape conforming isolation material is made of a material selected from the set consisting of: polyolefin, neoprene, polyvinyl or polyester.

5. The device of claim 1 wherein the shielding material is incorporated onto an inner surface of the second shape conforming isolation material.

6. An implantable medical device comprising:
   a sealed housing made of a biocompatible conductive metallic material;
   circuitry positioned within the housing;
   at least a first heat-shrink shape conforming isolation material encapsulating a portion of the circuitry to shield the portion of the circuitry from the housing;
   a thin layer of conductive shielding material surrounding the first shape conforming isolation material; and
   a second shape conforming isolation material encapsulating the layer of shielding material.

7. The device of claim 6 wherein the shape conforming isolation material substitutes for a frame for holding the circuitry.

8. The device of claim 6 wherein the shape conforming isolation material is selected from the set consisting of: polyolefin, neoprene, polyvinyl or polyester.

9. The device of claim 6 wherein the shielding material is incorporated onto a surface selected from the set consisting of: an inner surface of the second shape conforming isolation material or an outer surface of the first shape conforming isolation material.

10. The device of claim 6 wherein the second shape conforming material has a higher dielectric constant that the first shape conforming material.

11. The device of claim 6 wherein the first shape conforming material is mechanically stronger than the second shape conforming material.

12. An implantable medical device comprising:
    a sealed housing made of a biocompatible conductive metallic material;
    circuitry positioned within the housing;
    at least a first shape conforming isolation material adhered to an inner surface of the housing to shield a portion of the circuitry from the housing;
    a thin layer of conductive shielding material surrounding the first shape conforming isolation material; and
    a second shape conforming isolation material encapsulating the layer of shielding material.

* * * * *